United States Patent [19]

Ford, Jr. et al.

[11] Patent Number: 4,648,715

[45] Date of Patent: Mar. 10, 1987

[54] ELECTROPHORETIC LIGHT SCATTERING WITH PLURAL REFERENCE BEAMS, APPARATUS AND METHOD

[75] Inventors: Norman C. Ford, Jr., Amherst, Mass.; Bennie R. Ware, Marietta, N.Y.

[73] Assignee: Langley-Ford Instruments a division of Coulter Electronics of N.E., Amherst, Mass.

[21] Appl. No.: 592,829

[22] Filed: Mar. 23, 1984

Related U.S. Application Data

[63] Continuation-in-part of Ser. No. 415,581, Sep. 7, 1982.

[51] Int. Cl.$^4$ ............................................. G01N 21/00
[52] U.S. Cl. ..................................... 356/344; 356/343
[58] Field of Search ................ 356/28, 28.5, 344, 349, 356/343, 354, 356

[56] References Cited

U.S. PATENT DOCUMENTS

| | | | |
|---|---|---|---|
| 3,732,014 | 5/1973 | Uzgiris | 356/344 |
| 3,766,048 | 10/1973 | Flygare et al. | 356/344 |
| 4,397,550 | 8/1983 | Matsuda et al. | 356/349 |

OTHER PUBLICATIONS

McDonnell et al., "Multiple-Beam Laser Velocimeter: Analysis and Applications", Applied Optics /vol. 19, No. 17/ Sep. 1, 1980, pp. 2934–2939.

Primary Examiner—R. A. Rosenberger
Assistant Examiner—Crystal D. Cooper
Attorney, Agent, or Firm—Andrew F. Kehoe

[57] ABSTRACT

Multichannel electrophoresis apparatus employing electrophoretic light scattering as a means for characterizing the particles under study. The apparatus is characterized by the ability to measure light scattered simultaneously using a plurality of local oscillators incident at different angles from the same population of particles being subjected to electrophoresis. The apparatus is used with data processing means to analyze the large amount of scattering data which provide information on electrophoretic mobility, particle size, particle charge, electrophoretic mobility, zeta potential. An important aspect of the new apparatus is a markedly improved capability to segregate data related to diffusion effects from data relating to heterogeneous effects.

10 Claims, 11 Drawing Figures

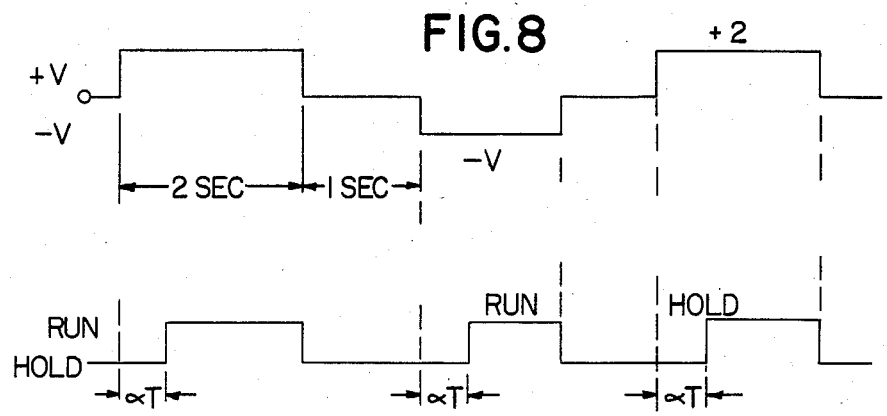
FIG. 8
FIG. 9
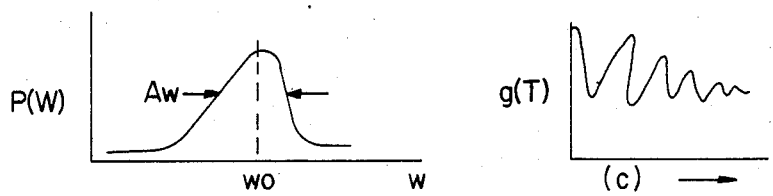
FIG. 11
FIG. 10

ELECTROPHORETIC LIGHT SCATTERING WITH PLURAL REFERENCE BEAMS, APPARATUS AND METHOD

RELATED APPLICATION

This application is a continuation-in-part of U.S. patent application Ser. No. 415,581 filed by Norman C. Ford, Jr. on Sept. 7, 1982.

BACKGROUND OF THE INVENTION

The invention relates to improved apparatus for measuring, by light-scattering techniques, the characteristics of particles subjected to electrophoretic processes.

In general electrophoretic light scattering (ELS) is a process described as follows: Particles, light-scattering entities often molecular in nature, are dispersed in a transparent liquid medium which is placed between positive and negative electrodes and subjected to an electric field. Depending upon the size, shape, and electronic natures of these particles, they tend to react differently to the electric field, particularly in terms of movement, and this reaction can be interpreted in analytically-useful ways by the use of light scattered from the particles.

There is a large body of literature relating to such work. A chapter entitled "Electrophoretic Light Scattering" by Ben R. Ware and Daniel D. Haas which appeared in Fast Methods in Physical Biochemistry and Cell Biology edited by R. I. Sha'afi and S. M. Fernandez (Elsevier, 1983) gives a good bibliography of literature relating to, and forming the basis for, the electrophoretic light scattering art.

Electrophoretic light scattering measurements utilizing a doppler shift detected by comparing the scattered light to a "local oscillator" (which is light from the original source which has not undergone scattering and may be viewed as a light-scattering control or standard against which other scattered light is referenced) have evolved in recent years. One advantageous embodiment of a doppler-type apparatus is described in a co-pending patent application Ser. No. 415,581 entitled Light Scattering Apparatus and Method and filed on Sept. 7, 1982 by Norman C. Ford.

A number of patents have been published relating to electrophoretic measurements. Some of these, including U.S. Pat. Nos. 3,984,533; 4,011,044; 4,102,990 and 4,217,195; are among those listed in a Summary Report entitled Laser Doppler Spectroscopy Technology dated October 1980 and prepared by the Technical Marketing Operation of the General Electric Company.

Electrophoretic light scattering (ELS) has been applied with success to the characterization of biological particles from small proteins to large living cells. A principal advantage of the procedure has been the ability to characterize the properties of many particles at the same time. Nevertheless, it has been difficult to distinguish, in some cases, between random movement of particles being characterized and movement which is more characteristic of the electrophoretic mobility.

Particles to be evaluated in any test sample, will usually be heterogeneous in some important respects. For example, particles in a sample system will probably differ with respect to size-related polydispersity and electrophoretic mobility in a given electrophoretic environment. In many samples, and especially those with large particles such as blood cells, it becomes particularly difficult to analyze scattered light information and interpret it in terms of the characteristics of all particles in the population being measured.

Thus it has remained to find a more convenient and practical way to vary the conditions of light scattering effects under a large variety of conditions so that the various light scattering effects can be more definitely evaluated and related to the nature of particle sample under study.

SUMMARY OF THE INVENTION

It is a principal object of the present invention to present an apparatus for characterizing electrophoretic light-scattering, call "ELS", from particles being characterized, and most particularly an apparatus that is capable of distinguishing heterogenous electrophoresis effects from diffusion effects on particles subjected to an electrophoretic field.

Another object of the invention is to provide data-processing means whereby the superior detection characteristics of the electrophoretic apparatus can be rapidly analyzed.

A further object of the invention is to provide a particularly advantageous optical arrangement for transmitting light to the sample cell in such a way as to allow optimal processing and analysis of light leaving the sample cell.

Still another object of the invention is to provide a rapidly-replaceable electrophoretic cell means which further complements the capability of the invention to provide rapid comprehensive testing.

Still other objects of the invention will be recognized by those skilled in the art on their reading of this disclosure.

"Particles" as described herein are defined as light-scattering entities in a fluid medium. They are frequently molecular species or other such entities not always strictly viewed as particulate in nature. Most work has been done with light-scattering particles in the range of from 0.1 to one micrometer in average diameter, but there is no reason to believe that successful measurements cannot be carried out with other particles, e.g. particles of a magnitude larger or smaller than the indicated range. A range from 0.01 to 30 microns is satisfactory.

The above objects have been substantially achieved by construction of electrophoretic light-scattering, or ELS, apparatus of the Doppler shift-measuring type which utilizes a highly advantageous multiple array of scattered light receptors in combination with means to introduce a local-oscillator portion of the light source which is not scattered during passage through an electrophoretic sample cell. Other light detecting means are so placed as to receive light scattered at a plurality of angles from the particles being characterized. In order to provide a simultaneous analysis of the immense amount of data which such an apparatus may provide, a computer control means is advantageously used to aid analysis and also to control and modulate the electrical supply to the electrophoretic cell. Such light-evaluating apparatus are already available in commerce and are readily adapted, with manufacturer's instruction, for use with the present invention. One such device is sold by Langley Ford Instruments of Amherst, Mass. under the designation the 1096 digital correlator.

The new apparatus may be used with data processing means to analyze scattering data and provide information on electrophoretic mobility, particle size, particle charge, electrophoretic mobility and zeta potential.

The light scattered at different angles (and the reference beams which act as local oscillators) is received on different photodiodes. It is convenient to use photodiodes with a built-in operational amplifier to improve the signal/noise ratio. Such photodiodes are readily available and can be obtained from EGG company under the designation HUV-1100BQ. The output signals from the output of the photodiodes are readily processed on the available digital correlators such as described above.

The usual computer control procedure can be carried out by those of ordinary skill in the ELS art following the instructions of the Equipment supplier and, preferably, utilizing readily-available computer hardware and software. Alternately, software can be developed by a capable programmer familiar with the ELS art.

It is to be understood that the apparatus is readily configured for utilizing differently shaped sample cell chambers, different laser sources; different light beam configurations, as long as they are compatible with the selected sample chamber; or including beams crossing one another in the sample chamber. Moreover, the apparatus allows an operator to view the scattering volume and to move that volume with respect to the light source to suit a particular experiment.

It is to be stressed that it is important to carry out the multi-angular testing on a given sample simultaneously. This is not only because of the relative inconvenience of conducting multiple tests. For example, in many materials to be tested, there will be sufficient statistical variations, e.g. as to size, occurring among particle populations of sequential "cell loads" of the same material to make interpretation of results under various test conditions difficult or impossible. However, if those measurements are taken from the same cell load, the unavoidable statistical variation in sample loads is avoided.

THE DOPPLER SHIFT

In ELS processes of the type described in this application, one measures electrophoretic velocities through the Doppler shifts of laser light scattered from the particles. By analogy with sound waves from a source moving towards the detector at speed v, the Doppler shift of the frequency for either light or sound is given by:

$$\Delta \nu = (v/c)\nu_o$$

where $\nu_o$ is the original frequency in the source's inertial frame of reference and c is the characteristic speed of the wave (i.e., the speed of light for light scattering). If the source is moving at some angle $\theta$ with respect to the detector, the magnitude of the Doppler shift is diminished by a factor of sin $\theta$.

The fact that the Doppler shift impressed upon the scattered light by a moving particle is directly proportional to that particle's velocity may give the misleading impression that the light scattering spectrum will simply be a histogram of the sample particles' instantaneous velocities. In addition to the electrophoretic drift, the particles undergo the jostling motions of random Brownian diffusion. These random components have velocities which are orders of magnitude greater than the electrophoretic drift velocities at the usual electric field strength. However, in actual practice, the electrophoresis causes a well-characterized spectral peak at the proper Doppler shift frequency, with a linewidth dependent upon a particle's diffusion constant. This primary dependence of the spectral shift upon electrophoresis rather than upon random motions can be reconciled with the Doppler shift explanation by interpreting the Doppler shift in classical terms as a continuously increasing phase shift impressed upon light of the original source frequency by the particle's motion, causing an apparent frequency shift in the observed light. Only those motions which carry the particle a substantial fraction of the wavelength of the illuminating light can cause a noticeable change in the time required for successive crests of the scattered light wave to reach the detector, thereby affecting the perceived frequency of scattered light seen by the detector. Individual steps in the random walk executed by the sample particle are much too small (only a few angstroms) to be detectable with light of optical wavelengths. The cumulative effects of many steps in a particle's diffusion are only noticeable as a secondary contribution to the electrophoresis peak in an ELS spectrum because diffusion broadens the distribution in times required for sample particles to migrate roughly a wavelength of light while being forced through solution by an applied electric field.

INTERFERENCE PHENOMENA AND THE PRINCIPLE OF BEATING

Although in theory the Doppler shift produced by an electrophoresing particle could be detected directly, this shift is so small (about 100 Hz shift on a carrier frequency of about $10^{15}$ Hz) that no optical filters of sufficient resolution are available. The only practical way to detect the shift is by optically beating the Doppler-shifted scattered light with a portion of the original illuminating light. This situation can be analyzed by simply considering the simultaneous observation of light scattered from two particles: (1) the test particle which is moving under the influence of the electric field and might also be executing random Brownian movement or any other motion of interest; and (2) a stationary particle, referred to as the local oscillator, which might be rendered immobile by attachment to the wall of the sample chamber. Most of the important effects seen in light scattering experiments can be explained with the aid of this simple system.

The oscillating electric field of the illuminating light forces the electron distributions of each of the molecules constituting these two model particles to oscillate slightly about their normal motion with respect to their associated atomic nucleii. In accordance with the classicial Drude model (The Theory of Optics, Longmans Green & Co., NY, 1907), the frequency of the electrons' oscillations is the same as the driving frequency of the illuminating light seen in the rest frames of each particle; and the phase of the electrons' oscillations with respect to the light's electric field oscillations is determined by the proximity of the light's frequency to the resonance frequencies of the electrons (i.e., the absorption frequencies of the particles). These electron oscillations in turn cause the particles to appear as secondary sources radiating light of the same frequency as the incident light, although with amplitude and phase shift with respect to the illuminating light as prescribed by the particles' positions and constituent matter.

If the two particles are separated by a distance d, then their far-field intensity pattern is a series of interference maxima and minima at scattering angles determined by the interparticle separation, d, and the wavelength of the light. The interference pattern is caused by the phase difference in the superposition of the oscillating electric fields emanating from the two particles. Maxima of the interference pattern are located at observation angles for which the distance the light travels from the source by way of one particle to the detector is precisely an integral number, m, of illuminant wavelengths greater than the distance from the source via the other particle to the detector:

$$\sin(\theta \text{ intensity})_{\text{maximum}} = \frac{m \text{ (wavelength)}}{d}$$

Suppose the test particle moves slightly farther away from the stationary local oscillator, perpendicular to the direction of the illumination. This increase in d, the interparticle spacing, causes a decrease in the angular separation of the far-field interference maxima and minima. Upon sufficient test particle motion, a photodetector originally placed to observe an interference maximum would be receiving a minimum of interference intensity due to the overall contraction of the interference pattern. Monitoring the photodetector's output discloses a regular sinusoidal oscillation in photocurrent with time as the test particle moves at constant velocity away from the local oscillator, and successive interference maxima and minima of scattered light intensity sweep across the photosensitive region of the detector. This oscillation of the detector's output can be exemplified in the photocurrent-versus-time plot. The frequency of photocurrent oscillation is identical to the Doppler shift appropriate for the test particle's velocity; but the stationary local oscillator is needed to achieve this scheme of "beating", or "heterodyning", the test particle's scattered light. Presence of the local oscillator converts the Doppler-shifted light of constant amplitude from the moving test particle into a total scattered light flux of varying intensity at the detector, indirectly rendering the miniscule Doppler shift detectable.

A particle moving upwards cannot be distinguished from a particle moving downwards by the intereference method, because the signal modulation is generated simply by the particle going from positions producing scattering maxima to positions producing scattering minima for either direction of travel. However, direct determination of the Doppler shift would readily show an increased light frequency observed for a particle moving down toward the detector, but decreased frequency for a particle moving upward. The insensitivity of the "beating" method to the sign of direction of the observed particle's motion is called the Doppler ambiguity, from a similar problem encountered in radar applications. However, by shifting frequency of local oscillator, one can remove Doppler ambiguity.

ANGULAR DEPENDENCE

A detector receiving light scattered perpendicular to the illumination direction ($\theta$-90°) would observe an interference maximum replacing a minimum for $\lambda/2$ translation of the particle perpendicular to the illumination direction. But note that for the same detector placement to receive 90° scattering, no change in interference intensity is observed for particle motion at 45° to the illumination direction. This is because, for any scattering angle, the loci of points of equal optical path length from the illuminator's phase via the point of interest to the detector's phase front constitute lines (actually, planes in three-dimensional space) which bisect the scattering angle. Motions which carry a particle from one point to any other within the same plane of constant optical path length will not alter the relative phases of the scattered light intensity reaching the detector from the particle and the local oscillator. Only the component of particle motion perpendicular to these planes will cause modulation of the observed scattering intensity and result in a detectable signal change. If the test particle is originally in a plane causing an interference maximum at the detector, translocation of the particle by:

$$\text{scattering plane spacing} = \frac{\lambda}{2 \sin (\theta/2)}$$

(wherein $\lambda$ is the wave length and $\theta$ is the angle of scatter normal to the original plane) will carry the particle to the next plane for maximum scattering intensity and the signal at the detector will pass from a maximum through a minimum to another maximum as a result of such motion. The separation between planes of equal scattering intensity is determined only by the wavelength of the illuminant and by the scattering angle selected for observation by the arrangement of the detector with respect to the illumination beam, not by any properties of the scattering particles. This definition of scattering plane spacing is a statement of the effect known as the Bragg condition.

The periodic spacing of these planes permits them to be succinctly characterized by a vector called the K-vector or scattering vector, whose amplitude is inversely proportional to the spacing of its associated planes and whose direction is normal to that set of planes:

$$\vec{K} = (4\pi/\lambda) \sin (\theta/2) \hat{K}$$

where $\hat{K}$ is the unit vector directed normal to the planes. The K-vector is simply the difference between vectors describing the illuminating beam, $\vec{k}_o$, and scattered light, $\vec{k}_s$:

$$\vec{K} = \vec{k}_o - \vec{k}_s$$

whose directions coincide with the propagation directions of their respective light waves (i.e., normal to their respective wavefronts) and whose amplitudes are inversely proportional to their respective wavelengths:

$$\vec{k}_o = (2\pi/\lambda_o) \hat{k}_o$$

$$\vec{k}_s = (2\pi/\lambda_s) \hat{k}_s$$

in the same fashion as the K-vector is defined by the wavelength (i.e., periodic spacing) and normal of its planes of equal scattering intensity. As mentioned earlier, the Doppler wavelength shift induced by electrophoresis of most sample particles is only one part in ten billion, so the wavelength of the scattered light is typically considered to be identical to the illuminant's wavelength for most purposes:

$$\lambda_o \approx \lambda_s$$

Since the illuminant and scattered light wavelengths and k-vector amplitudes are nearly equal, the amplitude of the K-vector is determined solely by the angular difference of the constituent light vectors which gives rise to sin ($\theta/2$) factor of Equation A.

Diffusion

In the above discussion, the test particle has been assumed to be moving at constant speed with respect to the local oscillator, so that the detected signal indicates intensity modulated at only a single frequency given by the appropriate Doppler shift. But in reality all matter possesses thermal energy which is manifested by submicron particles suspended in water as random Brownian motion. This diffusional motion superimposes a random walk on the persistent directed motion of an electrophoresing particle. An ensemble of electrophoresing particles initially located on one plane of maximum scattering intensity will require a distribution of times to reach the neighboring plane of maximum scattering intensity, resulting in a diffusion-broadened spectral peak at the Doppler shift. The peak width caused by diffusion exhibits an angular dependence proportional to the square of the amplitude of the scattering K-vector ($K^2$ dependent) whereas the Doppler-induced peak shift is only linearly proportional to $|\vec{K}|$ (K dependent). Thus the analytical resolution of the technique may be improved, when diffusion is a significant contribution to the linewidth, by working at a lower scattering angle as suggested by Ware and Flygare. (Chem Phys. Lett. 12 81-83).

Although these angular dependences can be derived mathematically, they are rationalized via the previous discussion of the scattering planes' separation. Diffusion is characterized by short, jerky motions in random directions which seldom carry the particle very far away from its starting position. Spectra obtained at small scattering angles (small $|\vec{K}|$, large plane spacing) respond primarily to the long-range directed motion of electrophoresis and are only slightly affected by the random Brownian motion. But at large scattering angles (large $|\vec{K}|$, small plane spacing), these random motions of diffusion are increasingly likely to carry a particle from one plane to the next, making the diffusion broadening larger in comparison to the electrophoretic Doppler shift.

Sample Heterogeneity

A sample may be heterogeneous in two important respects: (1) size (polydispersity); and (2) electrophoretic mobility. A polydisperse sample of small particles often exhibits peak broadening due to the dependence of electrophoretic mobility upon particle radius. A sample of large particles with identical surface charge densities may not show any direct evidence of polydispersity in a single ELS spectrum because all of the particles would be expected to electrophorese at the same velocity regardless of size. Comparison of ELS spectra collected at various angles often permits some inference about the behaviors of different-sized particles in a size-polydisperse sample, because particles much smaller than the illuminant's wavelength scatter an equal amount of light in all directions about the oscillation axis, whereas light scattered from different portions of a large particle will destructively interfere, causing the scattered intensity from large particles to taper off at higher scattering angles.

The spectrum from an electrophoretically heterogeneous sample is a superposition of Lorentzians centered at various frequencies, corresponding to the electrophoretic mobilities of each of the sample particles. Due to the small diffusion coefficients of large particles such as blood cells, their ELS spectra can usually be interpreted as histograms of the cells' electrophoretic mobilities; and surface-charge-density polydispersity is the principal cause of peak width, rather than diffusion. If the difference in electrophoretic mobilities is insufficient to produce individually resolvable peaks, apportionment of a single inhomogeneously broadened peak into its constituent population contributions is exceedingly difficult. Measuring peak width for several scattering angles is a good test for deciding whether a peak is broadened by diffusion or by electrophoretic mobility dispersion since width due to the latter is linearly proportional to K (i.e., sin ($\theta/2$)). Also, a linear increase in peak width with greater applied electric field may be an indication of electrophoretic heterogeneity.

IN THE DRAWINGS

FIGS. 8, 9, 10 and 11 illustrate typical light-scatter sampling cycles and some parameters measured thereby.

Figure 1:
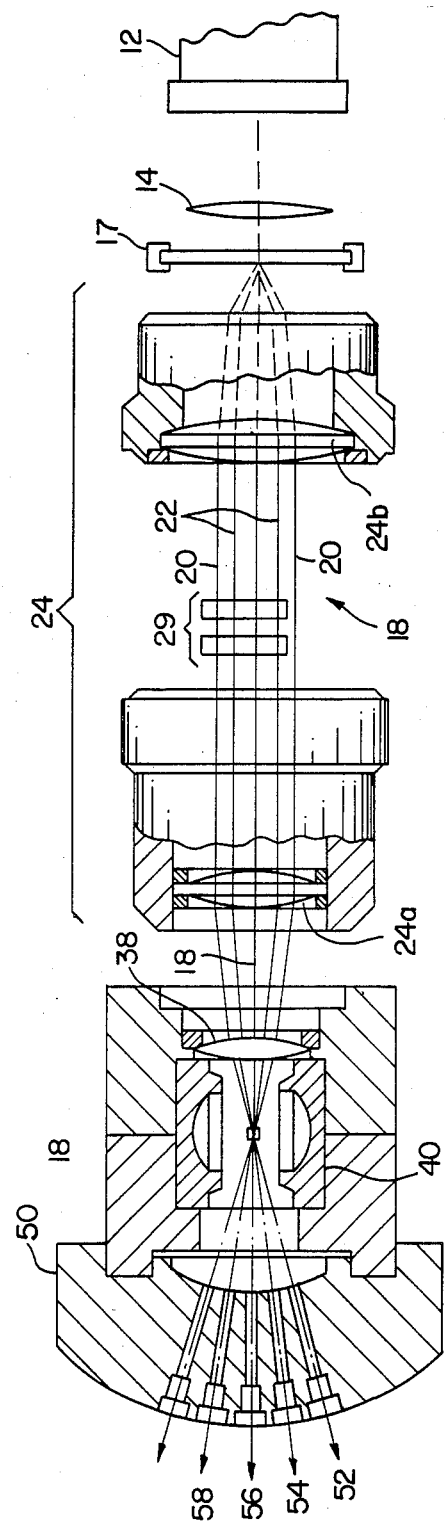
FIG. 1 is an optical schematic, partly schematic, and partly in section of one electrophoresis light scattering apparatus constructed according to the invention.

FIG. 1 illustrates electrophoretic apparatus 10 which comprises a laser light source 12, through a focussing lens 14 and a diffraction grating 17. The diffraction grating 17 is advantageously selected such that one of the second order light beams schematically illustrated as 18 is the more intense than the other light beams 19, 20, 21 and 22 which serve as local oscillators. The light leaving grating 17 is further focussed by an appropriate lens system 24 to collimate and focus the light. Lens system 24 pair consists of two 50 mm F1.7 camera lens 24a and 24b.

The diffraction grating 17 produces a second order light beam 18 which is more intense than each of the other four light beams (19, 20, 21 and 22). This second order beam (18) is called the main beam. The four other beams (19, 20, 21 and 22) are called reference beams and act as local oscillators (19, 20, 21 and 22). As described below, the main beam (18) passes into the sample cell (40) with an intensity four approximately orders of magnitude greater than each of the four reference beams (19, 20, 21 and 22). As a consequence, most of the light scattered by particles in the sample cell (40) is scattered from the main beam (18). The light scattered from the main beam is what is measured.

Each of the four reference beams (19, 20, 21 and 22) acts as a local oscillator against which the light scattered from the main beam (18) in the sample cell (40) is referenced. A grating 17 with 250 lines per mm is convenient. Such gratings are known in the art and may be purchased from a number of suppliers including the American Holographic company.

A 4-beam attenuator 29, consisting of two polaroid sheets, is placed within lens system 24. It is used to produce a polarized light output which is, in a typical application, reduced to about $10^{-4}$ of the light incident thereon. The attenuator serves to adjust downwardly the intensity of oscillator beams with respect to the main reference beam. All beams have been maintained in strict coherence; thus the collimated light rays leaving lens array 24 may enter an electrophoresis sample cell module 40 through a focusing lens 38 which is characterized by the ability to focus light over an annular range of 30 degrees with minimal spherical aberration. A component of the local oscillator beams will, of course, proceed directly through the center of cell module 40 and be used as the local oscillators, or reference beams.

Thus each light beam is passed into photosensitive receptors such as photodiodes 52, 54, 56 and 58 of sensor array 50.

Figure 2:
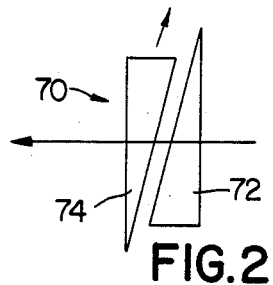
FIG. 2 is a schematic diagram of a frequency shifter useful with the apparatus of the invention.

Also illustrated in FIG. 2 is an optional frequency-shifter means 70 comprising a stationary prism 72 and a moveable prism 74. Prism 74 is moved at a constant velocity, v, along a path such that the distance separating the wedges is maintained constant and very small.

Figure 3:
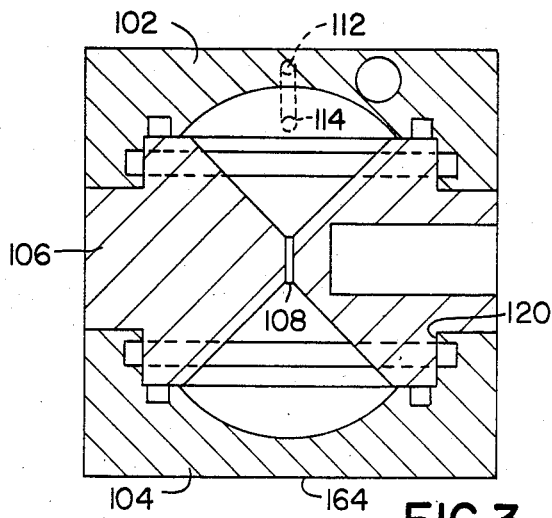

FIG. 3 illustrates sample cell 40 which is comprised of electrode-bearing member 102 electrode-bearing member 104 and the cell insert member 106. It is to be noted that member 106 should be formed of clear cast acrylic resin, ASTM D702. The electrophoretic sample-holding cell itself, i.e. aperture 108 of cell insert member 106 must be formed with the utmost attention to obtaining a smooth surface. Low-speed, optical polishing with rouge in a grease binder, with a reamer, or with a special buffing tool of the type known in the art is recommended. It has been found useful to apply kerosene during polishing for cooling during this finishing step.

Figure 4:
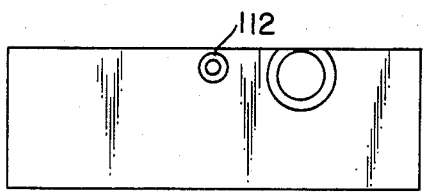
Figure 5:
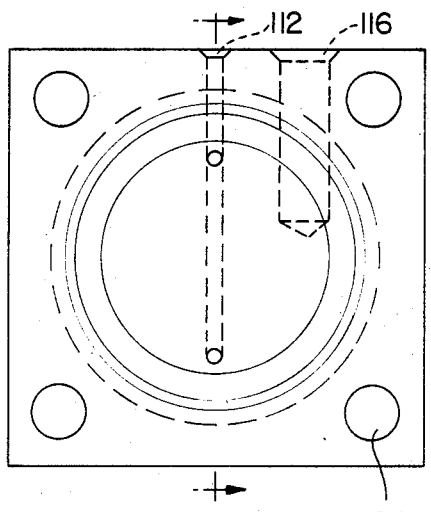

FIG. 4 is a top view of an electrode member 102 and FIG. 5 is a side view of this electrode member. The cell comprises electrode access taps 112 and 114 and one of the brass electrodes-bearing members 102 comprises a sample tap 116. An O-ring fits in grooves 120 and helps provide a good sealing action when the disposable cell insert member 106 is clamped between electrode bearing members 102 and 104 by bolts, not shown, through bolt holes 124.

Figure 6:
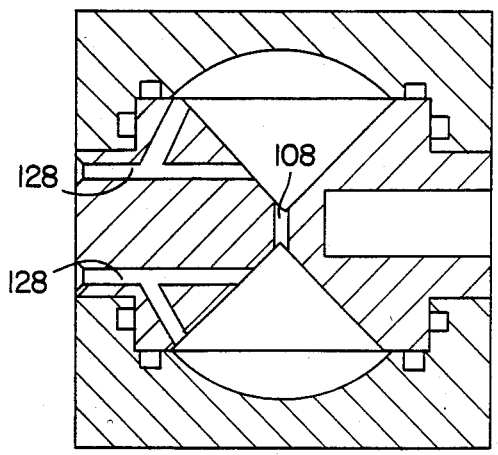
FIGS. 3, 4, 5, 6 and 7 illustrate a disposable sample cell element of the invention.
Figure 7:
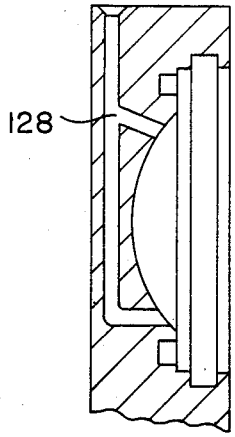

FIGS. 6 and 7 show clean out or flush passages 128 which allow cleaning of electrodes and flushing of the cells.

The cell 40 is readily disassembled and the cell insert member 106 is designed to facilitate replacement or refurbishment when this is practical. In this connection, it is noted that the interior surface of the aperture 108 of the cell 106 described herein is subject to an electroosmotic effect whereby the walls of the tube attract oppositely charged ions. This charge will effect the attitude and geometry of particles being studied and will interfere, in many cases, with the electrophoretic measurements being carried out on the apparatus. In order to avoid, or much reduce, any effect on the measurements, the wall of the aperture 108 of cell insert member 106 are coated with means to minimize surface charge under the solution conditions to be used. One suitable coating material is methyl cellulose.

Normally such coatings must be replaced frequently and this is one incentive for the construction of a disposable cell member. Proper coating of a cell many take several hours to several days. Thus referring again to FIG. 2, it is seen that electrode bearing members 102 and 104 may be readily separated from the cell insert member 106 which can then be quickly replaced with a pre-coated member without any substantial loss of operating time.

It is to be understood that, in the illustrated 4-angle analysis of the scattered light wave fronts, it will be convenient to operate a 1096-channel correlator as 4 simultaneous 256-channel correlators.

In such a system, FIGS. 8 and 9, may be used to illustrate an electrophoretic operating program relating voltages to time. The voltage will be, typically, between 50 and 300 volts and vary on the 2-second on, one-second-off cycle of FIG. 8 and the run-hold cycle of FIG. 9. In a typical situation, the dT equals N$\Delta$T, wherein N=number of channels used in correlator analysis of a light sample component; (256 in a preferred mode)

dT=0.256 seconds (typically)

$\Delta$T=correlator sample time, say $10^{-3}$ seconds

A typical analysis program, one standard in commercial apparatus, has the following components.

1. It measures the correlation function g (tau), as a function of tau. (See FIG. 10).

2. It analyzes via a Fourier transformation generating P ($\omega$) as a function of $\omega$, (See FIG. 11)

3. Thereupon $\omega_o$ and $\Delta\omega$ are found by fitting Lorentzian curves $$P(\omega) \alpha \frac{1}{(\omega - \omega_o)^2 + (\Delta\omega)^2} \text{ to}$$

to the curve of analysis item 2 above. The ($\Delta\omega$) is found for 4 different scattering angles $\theta$:

$$\Delta\omega = A \sin\frac{\theta}{2} + B \sin^2\frac{\theta}{2}$$

B is a measure of diffusion of the sample. A is a measure of the polydispersity characteristics of the particles of the sample subjected to electrophoresis. A is related to the mobility characteristics and distribution of mobilities. It is related to both size and charge properties.

Other approaches may be utilized in the assessment of the multiple wave fronts, but the subject approach is found to be adequate for most applications.

$\omega$=angular frequency, the characteristic variable of the power spectrum, P, resulting from the Fourier transformation of the autocorrelation function.

$\omega_o$=the central angular frequency shift due to the electrophoretic motion of the particles.

$\Delta\omega$=the broadening (around the central frequency shift, $\omega_o$) due to both diffusion and sample heterogeneity as discussed under the section herein on Diffusion and Sample Heterogeneity.

P($\omega$)=the power spectrum of the scattered light as a function of angular frequency, i.e. the Fourier transformation of g($\tau$)

It is also to be understood that the following claims are intended to cover all of the generic and specific features of the invention herein described and all statements of the scope of the invention which might be said to fall therebetween.

What is claimed is:

1. A process for the electrophoretic characterization of fluid-dispersed particles by measurement of electrophoretic light scattering from said particles, said process comprising the steps of (a) generating a light pattern, incident on said particles dispersed within an electrophoretic cell, which light pattern is characterized by (1) a relatively strong beam forming a principal source of scattered light and (2) a plurality of local oscillator beams of relatively low intensity compared to said strong beam, each of said relatively-low intensity beams being incident on said particles at angles different from each other and different from said strong beam, (b) directing said beams of relatively low intensity light, at a variety of angles, into a sample cell wherein the particles to be characterized are subjected to an electrophoretic environment, thence directing light from said cell onto detectors mounted at a plurality of angles around said cell;

(c) detecting and measuring, in each detector, a light from one of said plurality of local oscillator beams and light scattered from said strong beam by said particles within said cell at a plurality of angles, as said light leaves said cell, and (d) simultaneously evaluating light scattered at each said angle to distinguish electrophoretic characteristics of said dispersed particles from random diffusion characteristics of said particles.

2. A process as defined in claim 1 wherein said light source is passed through a diffraction grating such that a peripheral second order beams is more intense and thereupon attenuating the strength of all but one beam, said one beam serving as said strong beam.

3. A process as defined in claim 1 comprising the additional step of varying the frequency of said light entering said cell by passing through a frequency-shift device and evalulating light scattered from a given sample at different frequencies.

4. A process as defined in claim 2 comprising the additional step of varying the frequency of said light entering said cell by passing through a frequency-shift device and evaluating light scattered from a given sample at different frequencies.

5. Apparatus for evaluating the electrophoretic character of fluid-dispersed particles by measurement and analysis of light scattered from said particles, said apparatus comprising (a) means to direct a first beam serving as a relatively strong beam and a principal source of light to be scattered into an electrophoretic cell in which said particles are dispersed, (b) means to direct a plurality of additional light beams relatively weak relative to said first beam into said cell, said additional beams forming local oscillator means and being incident on said particles at different angles from said strong beam, and (c) light sensor means to simultaneously receive light scattered from said particles at a variety of preselected angles.

6. Apparatus as defined in claim 5 comprising, additionally electronic correlator forming means to evaluate said light scattered to distinguish electrophoretic characteristics from random diffusion characteristics.

7. Apparatus as defined in claim 5 comprising, additionally means to vary the frequency of light incident on said electrophoretic cell.

8. Apparatus as defined in claim 5 wherein said light is passed through an optical system comprising diffraction grating and light-attenuating means before said light enters said electrophoretic cell, said optical system forming means to provide oscillator beams of lower intensity and a principal beam of higher intensity.

9. A process as defined in claim 1 comprising the additional step of varying the relative frequency of said local oscillator and said strong beam.

10. A process as defined in claim 2 comprising the additional step of varying the relative frequency of said local oscillator beams and said strong beam.

* * * * *